(12) United States Patent
Murokh et al.

(10) Patent No.: US 6,776,340 B2
(45) Date of Patent: Aug. 17, 2004

(54) DUPLICATE LASER MARKING DISCRETE CONSUMABLE ARTICLES

(75) Inventors: Igor Y. Murokh, Santa Monica, CA (US); Alex Kerner, Pacific Palisades, CA (US)

(73) Assignee: Tri Star Technologies, A General Partnership, El Segundo, CA (US)

(*) Notice: Subject to any disclaimer, the term of this patent is extended or adjusted under 35 U.S.C. 154(b) by 47 days.

(21) Appl. No.: 10/164,140

(22) Filed: Jun. 4, 2002

(65) Prior Publication Data
US 2002/0179718 A1 Dec. 5, 2002

Related U.S. Application Data

(63) Continuation-in-part of application No. 09/360,233, filed on Jul. 23, 1999, now Pat. No. 6,429,889.

(51) Int. Cl.[7] .............................................. G06K 7/10
(52) U.S. Cl. .................. 235/454; 235/380; 235/381; 705/2; 705/22; 705/28
(58) Field of Search ................................ 235/454, 381, 235/380, 486; 705/2, 22, 28

(56) References Cited

U.S. PATENT DOCUMENTS

| | | |
|---|---|---|
| 3,657,510 A | 4/1972 | Rothrock |
| 4,595,647 A | 6/1986 | Spanjer |
| 4,753,863 A | 6/1988 | Spanjer |
| 4,906,813 A | 3/1990 | Gajdos |
| 5,030,551 A | 7/1991 | Herren et al. |
| 5,075,195 A | 12/1991 | Babler et al. |
| 5,091,284 A | 2/1992 | Bradfield |
| 5,111,523 A | 5/1992 | Ferlier et al. |
| 5,206,280 A | 4/1993 | Williams |
| 5,294,770 A | 3/1994 | Riddle et al. |
| 5,376,771 A | 12/1994 | Roy |
| 5,415,939 A | 5/1995 | Yeung |
| 5,489,639 A | 2/1996 | Faber et al. |

(List continued on next page.)

FOREIGN PATENT DOCUMENTS

AU        6079190        3/1991

*Primary Examiner*—Thien M. Le
*Assistant Examiner*—Allyson N. Trail
(74) *Attorney, Agent, or Firm*—Bruce A. Jagger

(57) ABSTRACT

A unique method of simultaneously marking both packaging and prepackaged articles such as tablets, pills, medical devices, and the like on the fly, without the deposition of ink or other marking materials on their surfaces, and without degrading the prepackaged articles or breaching the packaging. The markings can serve as unique identifiers for each individual marked article (serial numbers), as product identifiers (bar codes), or as tamper protection (positioning symbols), or the like. One product can be provided with all three types of marking, if desired. A radiation sensitive marking material such as titanium dioxide, for example, can be provided in both the article and a markingly associated window of packaging material. The article and the window together provide a marked pair. The amount of titanium dioxide in each element of the marked pair is effective to provide a mark when exposed to an effective amount of ultraviolet laser energy so that both elements of the marked pair are marked with the same mark at the same time. The energy is emitted in a predefined pattern so as to define the desired marking pattern in each of the window and the article. Marking is effectively instantaneous, thereby permitting the target prepackaged articles to be marked while in motion to efficiently and inexpensively provide very high marking rates. Articles can be sterilized and packaged in a clean room, and then removed from the clean room to some other site where marking of both the article and the package can be accomplished.

37 Claims, 7 Drawing Sheets

U.S. PATENT DOCUMENTS

| | | |
|---|---|---|
| 5,501,827 A | 3/1996 | Deeney et al. |
| 5,560,845 A | 10/1996 | Birmingham et al. |
| 5,568,177 A | 10/1996 | Talvalkar et al. |
| 5,637,244 A | 6/1997 | Erokhin |
| 5,650,209 A * | 7/1997 | Ramsburg et al. ............ 428/43 |
| 5,697,390 A | 12/1997 | Garrison et al. |
| 5,698,119 A | 12/1997 | Geerke |
| 5,773,494 A | 6/1998 | Gusi |
| 5,777,305 A * | 7/1998 | Smith et al. ................ 235/380 |
| 5,789,466 A | 8/1998 | Birmingham et al. |
| 5,798,037 A | 8/1998 | Peacock |
| 5,845,264 A | 12/1998 | Nellhaus |
| 5,915,733 A * | 6/1999 | Schnitzer et al. ........... 283/108 |
| 5,916,943 A | 6/1999 | Heller et al. |
| 5,918,909 A * | 7/1999 | Fiala et al. .................... 283/61 |
| 6,098,892 A * | 8/2000 | Peoples, Jr. ................. 235/494 |
| 6,108,026 A | 8/2000 | Corbett |

\* cited by examiner

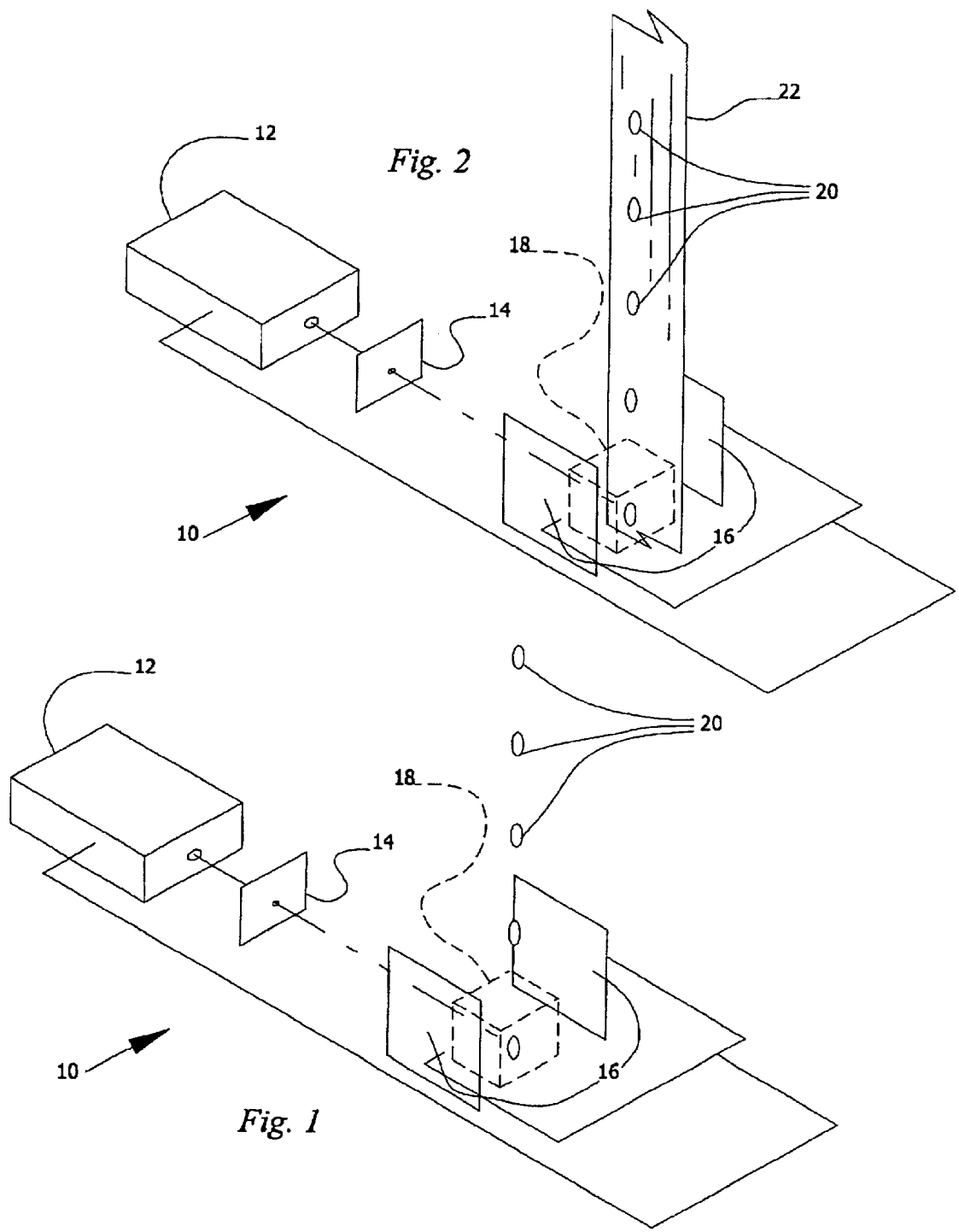

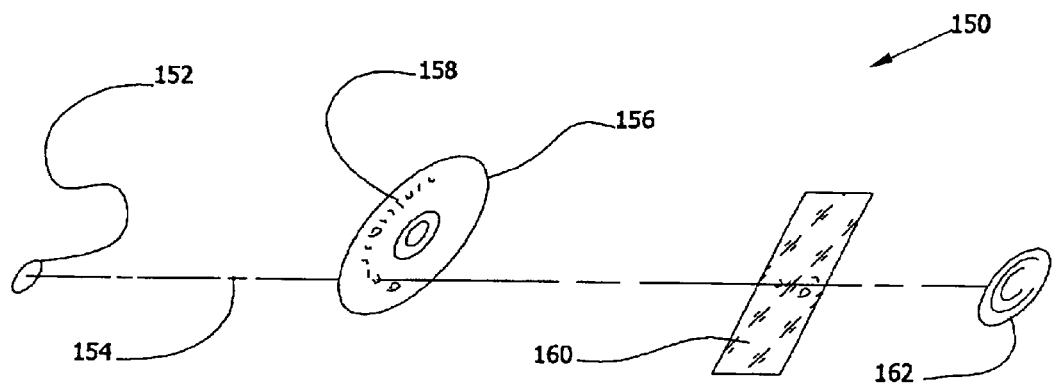
Fig. 3
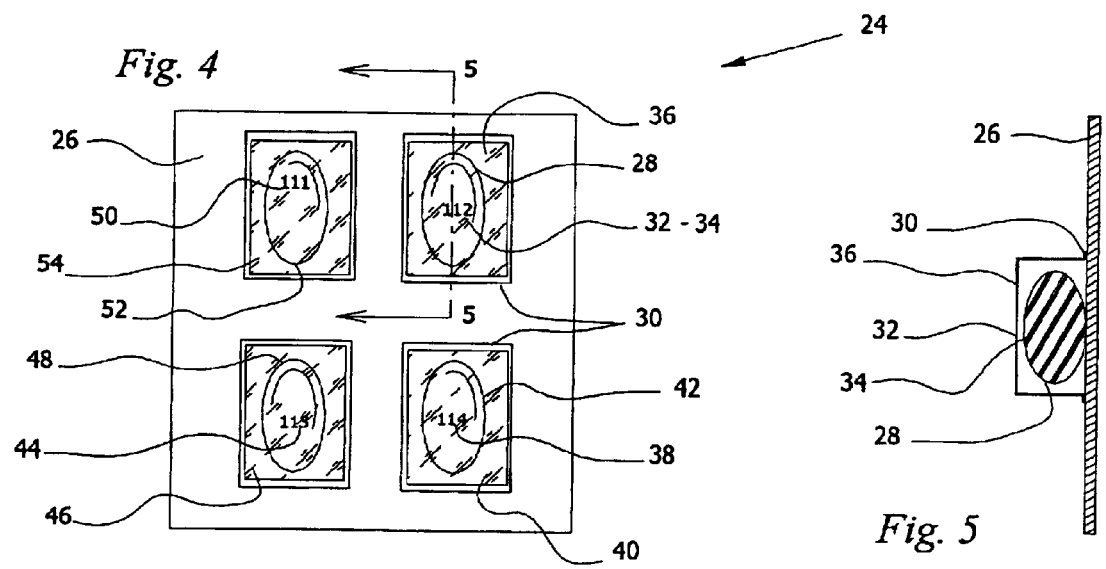
Fig. 4
Fig. 5

DUPLICATE LASER MARKING DISCRETE CONSUMABLE ARTICLES

RELATED APPLICATIONS

This is a continuation-in-part of Ser. No. 09/360,233, filed Jul. 23, 1999, U.S. Pat. No. 6,429,889.

BACKGROUND OF THE INVENTION

1. Field of the Invention

The invention relates in general to marked prepackaged articles, and to simultaneously marking both prepackaged articles and the associated packing with substantially identical non-destructive detectable markings. The detectable markings are formed in situ on both the articles and the packaging therefor without the deposition of any ink or other external marking material, and without degrading the articles or the packaging. The simultaneous application of a pattern of marking radiation, for example, ultraviolet laser energy, to such prepackaged articles through their associated packaging causes radiation sensitive material in the article and the packaging to change to a detectable form in the pattern of the applied radiation. Thus, both can be precisionly marked with identification, security, unique, or the like information such as serial numbers, bar codes, location indicia, and the like. Such simultaneous marking can be accomplished after the articles have been fully packaged, in single or multiple units in a single package, and while the prepackaged articles remain in continuous motion. The markings on the article are preferably detectable eye through a window in the packaging. Thus, the markings on both the packaging and the article are detectable at the same time.

2. Description of the Prior Art

The pharmaceutical industry today produces billions upon billions of human consumable articles such as therapeutically effective pills, tablets, jell-caplets, and the like. These articles contain a variety of different prescription and non-prescription drugs. Due to the variety and large production quantities of these consumable articles numerous potential health problems and concerns have arisen over the possibility of confusing one product with another, or deliberate substitution, or tampering. For example, there has become an increasing need to provide direct identification on each individual consumable article, particularly therapeutically effective articles, so their origins and contents can be traced in an audit, or after the occurrence of an incident of some kind. For example, this has been found to be very valuable for the elderly where over prescription problems can result, as described in Nellhaus U.S. Pat. No. 5,845,264. Nellhaus describes the application of bar codes directly to consumable drugs by utilizing conventional high resolution printing techniques. These techniques deposit selected amounts of a marking material, such as non-toxic or inert ink, directly on the surface of the drugs. A common technique is to apply food grade ink approved by the Food and Drug Administration with an ink jet or rotary wheel printer.

Individually marking each of a plurality of individual articles has many advantages. For example, the articles can always be identified and distinguished from other articles even when removed from their containers or packaging. In addition, consumable articles, for example, can always be distinguished from other non-pharmaceutical consumable articles such as candies, and the like. With the individual marking of each consumable article, serious life threatening mistakes can be avoided. Such individual marking is also advantageous because accidental overdose situations, and the like, can be more quickly diagnosed.

Ablative laser marking of tablets had been proposed previously. Gajdos U.S. Pat. No. 4,906,813 teaches treating tablets with a gas laser beam to induce marking by ablatively burning off layers of the tablets. Riddle U.S. Pat. No. 5,294,770 teaches drilling drug release ports in pharmaceutical tablets with a laser. Undesirably, in both of these teachings, the laser energy is provided at such a high concentration as to physically burn off material from the surface of the tablet, that is, ablatively remove a portion of the material from the tablet. The removal leaves voids that can readily be seen with a 5× or less powered microscope or lens. This ablation can cause many problems. Clear, sharp marking is difficult to achieve depending on the amount of chipping that occurs due to the ablative activity. In addition, the burning caused by the laser may chemically alter the remaining material of the tablet near the mark, which is highly undesirable in pharmaceutical applications. Thus, in order to make it feasible to mark consumable articles with a laser, a non-ablative method is needed.

Security concerns had previously prompted the proposal of numerous expedients, which purported to inhibit or eliminate tampering. Safety concerns require the processing, and, usually the packaging, of certain articles in a sterile environment, such as a clean room. Such security and safety concerns had substantially complicated the marking of articles.

Lasers are generally not presently used to mark consumable articles. Instead, the prior proposed expedients for marking pills utilized ink, frequently the ink jet process, wherein a precisely controlled amount of an edible or inert ink material was deposited directly on the surface of the pill in a predefined pattern. The prior equipment for marking pills was large, expensive, and required high maintenance. As such, the prior equipment was inherently less than perfect and introduced a significant cost increase in the production process, particularly when it was operated in a sterile environment.

Ink marking requires precise control of the objects in order to positively and accurately deposit the ink. This is troublesome since consumable articles, for example, are very small, and they must be mass produced. Individually marking each article at a cost effective rate has proven to be problematic. Production rates are limited because each article must be securely held in position relative to an ink depositing instrument. The production rate may also be undesirably reduced since each freshly marked article must not be disturbed for a particular period of time dictated by the drying requirements of the ink.

Another problem with ink marking technology is maintaining the precise location of the ink head to the article in order to apply the desired amount of ink. This is further complicated when the articles are not of a uniform size in a given batch or from batch to batch of the same or different products. A change in size or shape requires a retooling of the marking equipment. When this precise positioning is not adequately controlled, too much or too little ink may be applied, undesirably resulting in an increased scrap rate. These problems exist with ink imprinting procedures such as ink jets, stamps, rollers and the like.

Still yet another problem is that ink feed devices such as ink jet heads are inherently subject to clogging. Clogging not only increases maintenance costs, but when ink feeds clog during a marking production run, a large quantity of tablets or pills may have to be scrapped. A high scrap rate is highly undesirable.

However, one of the greatest drawbacks to utilizing ink technology to mark consumable articles is the cost associated with preparing the articles for marking. Contaminants, such as organic oils and the like, on the surface of the articles must be removed prior to marking. These contaminants undesirably reduce or eliminate legibility and durability of the ink marking. Their removal requires that special pre-treatment cleaning systems be incorporated into the process. Most pharmaceutical articles require the application of a coating of oil on their surfaces during processing, and this coating must be removed prior to marking with conventional ink techniques. Thus, in pharmaceutical applications, a special pre-treatment cleaning system is required prior to marking. The equipment used to accomplish the pre-treatment cleaning is undesirably large and expensive, and also requires high maintenance.

Given the above problems, the prior art ink based marking systems could achieve maximum production marking rates of only about 1,200 pills per minute, or 72,000 per hour.

Another drawback in utilizing ink based processes to mark consumable articles is that the ink dispenser must be close to or in direct contact with the surface of the articles to be marked. Because the prior art printing techniques required that the printing mechanism have direct access to the surfaces that were to be marked, products that had already been encapsulated in packaging materials could not be marked. It would be highly desirable to be able to mark such articles after they are encapsulated in packaging. This permits greater flexibility in production operations. Even sterile products that were packaged and then irradiated in the package for sterilization purposes, were marked before being packaged.

Another limitation of the prior art equipment is that the edible or inert marking material must satisfy Federal food and drug regulations. Thus, it would be very desirable to mark these articles without introducing any additional material.

When ultraviolet energy is absorbed by certain titanium dioxide containing materials, the titanium dioxide changes color. This phenomena has been successfully utilized to provide markings on various non-consumable objects such as wire insulation, electronic components, ceramics, glass, plastics, and the like. See, for instance, U.S. Pat. Nos. 5,501,827, 5,091,284, 5,415,939, 5,697,390, 5,111,523, 4,595,647, 4,753,863, 4,769,310, 5,030,551, 5,206,280, 5,773,494, 5,489,639, and 5,798,037, which describe the laser marking of non-consumable articles made from various materials.

Numerous materials have the capacity to change detectably and irreversibly when exposed to radiation, particularly when the radiation is in the form of a laser beam of ultraviolet radiation. See, for example, Gugger et al. U.S. Pat. No. 4,769,310 where many inorganic pigments are listed along with the color changes that occur in them as a result of exposure to radiation from an ultraviolet laser. The pigments are incorporated in the object that is to be marked. Laser energy, preferably near ultraviolet in the 0.25 to 0.38 microns range, is applied to or focused on the object, and the color change occurs in the form of the intended graphic symbols.

Articles had been conventionally marked as produced before being packaged. Where sterile packages were necessary or desired, this required that the marking facility be inside of a sterile environment, that is, inside of a clean room. This greatly complicated and increased the cost of the marking operation. The marking equipment and supplies had to be kept sterile, and the operators had to follow the procedures for maintaining a sterile environment. Those skilled in such arts recognized the need for a solution to these problems.

Those concerned with these problems recognize the need for an improved method of marking prepackaged articles.

These and other difficulties of the prior art have been overcome according to the present invention.

BRIEF SUMMARY OF THE INVENTION

One object of the present invention is to provide a method of simultaneously marking discrete prepackaged articles and the associated packaging without the deposition of ink or other marking material on the articles or the packaging.

Another object of the present invention is to provide a high speed method of simultaneously marking discrete prepackaged articles and the associated packaging such that the articles can be marked on the fly, that is, they can be marked while they are in continuous motion.

Another object of the present invention is to provide a method of simultaneously marking discrete articles and their associated packaging at higher resolutions than currently possible using ink deposition techniques such as ink jet printing, and the like.

Yet another object of the present invention is to provide a method of simultaneously marking discrete prepackaged articles and the associated packaging without breaching the packaging.

It is yet another object of the present invention to provide a method of marking prepackaged discrete consumable articles and the associated packaging that does not require a pre-treatment cleaning process or post-treatment curing process.

Still yet another object of the present invention is to simultaneously mark prepackaged discrete consumable articles without etching or physically degrading the articles.

As used herein, "consumable articles" are articles intended to be consumed, orally or otherwise, by a living being, human or non-human, for therapeutic purposes, including prescription, non-prescription and food supplements. Examples of such discrete consumable articles include pills, tablets, gel caplets, dissolving tablets, lozenges, and the like.

According to the present invention individual consumable articles and the packaging associated with them are simultaneously marked by the application of irradiation energy, and without the deposition of any ink or other external marking material, and without physically degrading the articles or the packaging. As used herein, a "non-deposited marking" is a marking in which no marking material, such as ink, paint or the like, is physically applied to an article or the packaging during the marking process. Physical degradation results when the amount or nature of the energy applied to an article or the packaging causes that article or the packaging to burn, melt, vaporize, or otherwise degrade leaving a crater or an otherwise visibly damaged area that is readily visible with an optical microscope having a magnification factor of 5× or less. Such physical degradation can also include chemical degradation that alters the therapeutic nature of the product. Therapeutic degradation is not necessarily visible, however, such degradation of therapeutic effectiveness can be detected by chemical or biological analysis. Chemical degradation occurs when the degradation is sufficient to materially impair the therapeutic effectiveness or other intended usage of the article. Trace degradation that has no material effect on the intended usage is not considered to be physical degradation.

The method of the present invention comprises selecting a radiation sensitive material (dopant) that changes to a detectable color when exposed to laser or other energy, and incorporating an effective amount of that radiation sensitive material into a visible layer of the articles that are to be marked. Generally, but not necessarily, the radiation sensitive material is in the outer layer of the article. Similarly, an effective amount of the same or a different radiation sensitive material is incorporated into a window of the packaging material that is markingly associated with the article. A plurality of articles can be packaged in one package, if desired. The prepackaged articles are then preferably placed in motion and, preferably, a sensing location is established at a predetermined location or marking zone relative to a source of marking energy, such as, for example, an ultraviolet laser energy. The sensing location detects the arrival of a prepackaged article in the marking zone and triggers the firing of the marking energy, for example, a laser. Alternatively, the laser or other energy source can be moved relative to the articles and fired when it is in the proper position to mark an article, or both can be in motion when the energy source is fired. The beam of energy can be moved, without moving the source, by the use of a suitable energy beam delivery system, if desired. Also, the firing of the energy source can be synchronized to the relative movement between the articles and the energy source by some means other than a sensor that detects the arrival of an article in the marking zone. For example, the mechanism can be synchronized so that the energy source fires every time a particular station is passed by an article feed mechanism whether there is a prepackaged article in position to be marked or not, or the like. Each of the prepackaged articles is individually and instantaneously exposed to a predefined pattern of marking energy, for example, laser energy, preferably while it remains in motion. For purposes of economy a mask is very efficient in defining the pattern. Other pattern definition means can be used if desired. The marking energy is absorbed by the radiation sensitive dopant in each of the prepackaged article and the associated window of packaging according to the predefined pattern, and the radiation sensitive dopant, for example, changes color to provide the required detectable marking. In general, the detectable marking is visible to the unaided human eye. The marking may, however, be such as to be detectable by alternative means such as exposure to ultraviolet light, machine readers such as bar code readers, and the like, if desired.

Various ultraviolet generating lasers that are suitable for use in marking objects according to the present invention are well known. See, for example, Gugger et al. U.S. Pat. No. 4,769,310, where a number of lasers are listed, together with the wavelengths of the output they are capable of generating. Such lasers are well known to those skilled in the art and need not be further described here.

Preferably, the graphic information that comprises the markings according to the present invention is applied using a mask. It is possible, however, to focus a laser beam and move the beam or the object so as to form the desired graphic.

Because the laser marking occurs substantially instantaneously (typically, 10 to 20 nanoseconds), the prepackaged articles can be marked while in motion at relatively high rates of speed. For example, the prepackaged articles can be placed in motion by a conveyor system as is commonly used in many mass production facilities. However, the laser marking occurs so fast that it is possible to mark the prepackaged articles as they fall vertically under the force of gravity, thus allowing marking to be accomplished as the prepackaged articles fall from a vertical hopper, or the like. Other means of projection, such as, for example, centrifugal force, air pressure, or the like can also be used to place the prepackaged articles in motion. The rate of the prepackaged article's movement should be synchronized with the cycle time or pulse rate of the pulsed laser or other radiation source. If very rapid pulse rates are available it may be desirable to feed the prepackaged articles at a rate that is faster than a mere gravity feed can achieve.

Significantly, no external marking material is applied to the articles or the marking window at any time. Clogging problems and drying time requirements inherent in the prior art ink marking systems are completely eliminated. Pretreatment cleaning systems and post-treatment curing processes are no longer necessary. The problems associated with precisely positioning and holding the article relative to the ink applicators of the prior art are also eliminated.

Precise positioning and holding of the prepackaged article relative to the source of marking energy, according to the present marking process, is not required, provided the marking window and the article are both at the proper location to be marked when the marking energy system is activated. All that is required is that the area of a prepackaged article and the associated marking window that are to be marked be positioned within a relatively large focal range and roughly normal to a source of marking energy. Exposure to the source of marking energy is controlled so that no physical degradation occurs. With the essentially instantaneous marking of the articles and associated packaging, marking production rates are significantly increased, compared to prior art ink deposition marking systems.

According to one embodiment in the consumable area, 24,000 pills can be marked per minute, equating to 1,440,000 pills per hour. This is a substantial marking rate increase compared to prior art ink jet or inked rotary wheel techniques. For instance, it is twenty times faster than the conventional prior art production rate of about 1,200 pills per minute.

Because the marking results from the response by the radiation sensitive dopant in the articles and packaging to the laser or other marking energy, articles can be marked when fully encapsulated in packaging materials that are at least semi-transparent to the marking energy. Generally low concentrations of radiation sensitive dopant are provided in the packaging window, and relatively higher concentrations are found in the article. The packaging receives the highest dose of marking radiation so the minimal amount of dopant present there responds strongly. The radiation is generally somewhat attenuated when it reaches the article, but the higher concentration of radiation sensitive dopant responds more strongly than the more dilute dopant in the window of packaging. In general, the mark in the window is not as strong as in the article. The layer of the article in which the marking develops need not be the outer layer of the article so long as the layer(s) on top of the marked layer are transparent to the radiation and the marking detecting means. The marking actually occurs in situ at and below the surface of the dopant containing layer. For the marking to be visible the layer, and those above it, must be transparent enough to the visible spectrum of light that the marking is visible. The layer need not be transparent. Because the marking is near the surface a colored layer that is opaque when its entire thickness is considered can still be sufficiently translucent for the marking to be clearly visible. Consumable articles, for example, are often white in appearance because of the presence of the pigment, titanium dioxide. Where there is sufficient pigment to color the object white, the absorption of the ultraviolet energy and the resultant marking, takes place very close to the surface so that the markings are clear.

Inorganic pigments such as those listed in Gugger et al. U.S. Pat. No. 4,769,310 are suitable for use according to the present invention. Such pigments, and the changes in the detectable characteristics of such pigments under exposure to radiation are well known in the art and need not be further described or listed here. Typically, the pigments absorb radiation energy in the near ultraviolet and change color. Various organic radiation sensitive pigments such as polyethylketone and polyethylsulphone also change color when subjected to such radiation. Where the object is intended, for example, for human internal consumption, the radiation sensitive material should be one that is generally regarded as safe. A list of compositions that are generally regarded as safe is published and is well known to those skilled in the art. Titanium dioxide, for example, is generally regarded as safe. The heavy metal containing pigments are generally not on the generally regarded as safe list.

According to a preferred embodiment, an effective amount of finely divided titanium dioxide is provided in the layer of the article that is to be marked. In this instance, the surface layer contains the titanium dioxide. When exposed to a predefined pattern of laser energy in the ultraviolet range of from about 380 to 190 nanometers, precisely marked articles are produced with virtually no scrap. The markings are generally black. The markings are embedded in the layer so they are not entirely on the surface where they might be subject to erasure. They are generally visible by reason of a light colored background. Titanium dioxide is conventionally present in numerous pharmaceutical tablets and jellcaps formulations, and the like. These products can be marked with a laser according to the present invention without changing the formulation of the product so that regulatory requalification is not required. The titanium dioxide in these formulations was often intended to function as a whitening agent for the articles, and not at all for the purpose of enabling laser marking of the articles. The inclusion of a small amount of titanium dioxide dopant in an otherwise clear window of packaging material produces a slightly milky appearance, but the markings on the article are generally still visible to the unaided eye through the window. It is possible, for example, to determine whether the markings on the article are in registry with those on the window.

Generally, it is preferred the titanium dioxide be comprised of the rutile crystalline form. Also, it is preferred that the titanium dioxide be substantially white.

The titanium dioxide particles should have average diameters of less than about 10 and preferably less than 5 microns. Particle sizes of less than approximately 2 microns average are preferred. Larger particles require the use of undesirably high energy pulses. Higher and longer pulses of energy risk physical degradation and can, in extreme situations, slow the process down. The maximum duration of the pulse increases approximately with the square of the particle diameter. The following formula can be used to approximately estimate the maximum duration of the pulse that can be tolerated before physical degradation occurs.

$$T = D^2 \rho C_p / \lambda$$

where T=pulse duration in nanoseconds, D=particle diameter in meters, $C_p$=the heat capacity of titanium dioxide (690.37 Joules per kilogram degree Kelvin), $\lambda$=the thermal conductivity of titanium dioxide (6.55 Watts per meter degree Kelvin), and $\rho$=the particle density (4,000 kilograms per cubic meter). Read literally, this equation produces an answer in seconds. For ease of use this is converted to nanoseconds. Pulses of longer duration than those indicated by this equation will result in the application of more energy than the titanium dioxide can absorb by itself. Pulses of shorter duration should be used to avoid damaging the target article. For a particle with an average diameter of about 0.5 microns the maximum pulse duration is approximately 100 nanoseconds. As will be understood by those skilled in the art, several approximations are made in the above equation which preclude relying on it to determine anything other than the approximate order of magnitude of the maximum pulse duration times. For example, round particles are assumed. This is, of course, a very rough approximation for most particles. A constant particle diameter across all particles in the target is assumed. Again, this is only an approximation. There will always be some particle size distribution and agglomeration. This formula is useful in arriving at the order of magnitude of the maximum allowable pulse duration from which those skilled in the art can easily optimize a particular system. Effective marking can generally be achieved using significantly shorter pulses. For example, pulses of approximately 10 nanoseconds, an order of magnitude less than the maximum allowable duration, are generally effective in producing legible markings. The preferred optical pulse duration is from about 5 to 20 nanoseconds, but pulse durations of from approximately 5 to 200 nanoseconds are effective and can be employed, if desired. Some adjustment based on actual experimental results will generally be required to optimize the system. In general, the shortest pulse that is effective to produce a marking of the desired legibility should be used so as to minimize the risk of physically degrading the article. As the particle diameter increases more energy is required and the risk that energy will be dissipated by conventional heat and mass transfer processes beyond the pigment particles to the detriment of the article also increases substantially. For this reason the average diameter of the particles should be minimized.

The applied laser fluence or energy density (in Joules per square centimeter) is proportional to the diameter of the titanium dioxide particle. Without wishing to be bound by any particular theory it is believed that it should be assumed that the absorbed pulse of energy should be sufficient to heat the average pigment particle in the target article to its melting point. There should not be enough energy to change anything else in the target. Thus, where the pigment particles are the only part of the outer layers of the article that absorb ultraviolet energy, all of the energy should be absorbed by those particles. The following formula provides an approximation of the laser fluence (energy flow density) that is required.

$$F = 2\rho C_p D(T_m - T_a)/3$$

Where F=the laser fluence (energy flow density) in Joules per square meter; $\rho$=the particle density (4,000 kilograms per cubic meter); $C_p$=the heat capacity of titanium dioxide (690.37 Joules per kilogram degree Kelvin); D=the diameter of the particle in meters; $T_m$=2116 degrees Kelvin, the melting point of titanium dioxide; $T_a$=the ambient temperature in degrees Kelvin. For ease of use the energy density is generally converted to Joules per square centimeter, and the particle diameter to microns. This equation establishes an energy threshold for a system where the pulse duration has already been established. This equation generally provides an approximation that tends to be in the middle to lower end of the acceptable range of energy flux. It provides an approximate bench-mark from which those skilled in the art can easily optimize a particular system. In general an energy flux density of from approximately 10 to 0.1, preferably, 5 to 0.1 Joules per square centimeter is effective to form a satisfactory marking. Generally an energy flux density of from approximately 1 to 0.1 is most preferred. The minimum amount of energy that is effective to produce the desired marking should generally be used. For a particle with a diameter of about 0.5 microns the starting approximation for the laser fluence is in the order of 0.17 Joules per square centimeter.

The above equations yield the following calculated values for the particle diameters that are indicated in Table I below.

TABLE I

| Particle Diameter - D (microns) | Energy Density - F (Joules/cm$^2$) | Maximum Pulse Duration - T (nanoseconds) |
| --- | --- | --- |
| 0.10 | 0.03 | 4 |
| 0.25 | 0.09 | 25 |
| 0.35 | 0.12 | 49 |
| 0.50 | 0.17 | 100 |
| 0.75 | 0.26 | 225 |
| 1.00 | 0.34 | 400 |

The values given in Table I are order of magnitude values that provide those skilled in the art with a reliable starting point from which to optimize a particular system. Many different variables, not all of which are fully understood, enter into determining the optimum values for a particular system. For example, particle size distribution, the degree of pigment agglomeration that a particular processing system produces, and the like, all influence these values.

Energy density can generally be adjusted, optically or otherwise, through a wide range to a predetermined level as may be desired. The pulse duration, by contrast, is generally a fixed characteristic of the laser. When a laser is selected for the purposes of this invention, this inherent characteristic should be kept in mind. Most generally available ultraviolet lasers have pulse durations of less than 100 nanoseconds.

The titanium dioxide dopant should be present in the region that is to be marked in an amount ranging from approximately 0.25 to 5 weight percent, based on the weight of the layer. Preferably, the titanium dioxide is present in an amount of from about 1 to 3 weight percent in the article, and from about 0.25 to 1 in the window of packaging. The optimum density of the ultraviolet radiation on the window-article pair generally depends in part on the concentration of the titanium dioxide. Increasing the concentration of the titanium dioxide increases the risk of physical degradation. Below about 0.25 weight percent of titanium dioxide, the markings in the window tend to become faint. As the concentration of the pigment increases the clarity of the marking improves up to a point where the particles are so close together that there is a risk of degradation by reason of the concentration of absorbed energy. Where the concentration is low, on average the energy is absorbed, and the marking occurs, to a greater depth in the layer. The contrast is not as great where the concentration is so low that the marking occurs to a substantial depth in the layer. The radiation penetrates deeper into the article, and the resulting marking may not be fully detectable from the surface. The concentration of pigment or other dopant should be minimized as much as possible to avoid the necessity of using high energy densities consistent with achieving markings of acceptable contrast and crispness. Where the quality of the marking is not what is desired even at the maximum safe energy levels, the solution is to increase the concentration of the pigment rather than to degrade the window-article pair by increasing the energy level. Above a certain pigment concentration, however, the amount of energy required to generate an acceptable marking increases to an unacceptable level where degradation of the article is likely to occur. In general, pigment or other dopant concentrations of less than approximately 5 weight percent in the article are acceptable. It is assumed that the pigment is all of approximately of the same size and is equally distributed in the layer that absorbs the energy. Some processing procedures do not provide such optimum uniform distribution. Such systems should be optimized for the particular size and bulk distribution according to the teachings of the present invention.

The optimal wavelength for the ultraviolet energy is that at which the titanium dioxide absorbs energy most strongly. This is below about 400 nanometers. In general, lasers that emit ultraviolet light in the range of from about 380 to 190 nanometers are useful with those that emit energy at about 360 to 240 nanometers being preferred.

Preferably, for high volume production requirements the laser should have a pulse rate of from at least about 10 to about 1000, preferably, 20 to 400 Hertz. Pulse rate is to be distinguished from pulse duration. These are different characteristics of any given laser. Pulse rate generally defines the maximum production rate. Pulse rate indicates how many times the ultraviolet laser fires in one second, which is usually described in number of events per second (Hertz). Pulse duration indicates how long the laser is illuminated during each pulse, and is described in nanoseconds.

Other objects, advantages, and novel features of the present invention will become apparent from the following detailed description of the invention when considered in conjunction with the accompanying drawings.

BRIEF DESCRIPTION OF THE DRAWINGS

The present invention provides its benefits across a broad spectrum of marking prepackaged articles such as, for example, pills, tablets, capsules, medical devices, high value objects, and the like. While the description which follows hereinafter is meant to be representative of a number of such applications, it is not exhaustive. As those skilled in the art will recognize, the basic methods taught herein can be readily adapted to many uses. It is applicant's intent that this specification and the claims appended hereto be accorded a breadth in keeping with the scope and spirit of the invention being disclosed despite what might appear to be limiting language imposed by the requirements of referring to the specific examples disclosed.

Referring particularly to the drawings for the purposes of illustration only and not limitation:

FIG. 1 is a schematic view of a preferred embodiment consumable article laser marking system of the present invention.

FIG. 2 is a schematic view similar to FIG. 1 illustrating the use of a conveyor for the consumable articles.

FIG. 3 is a diagrammatic view of the radiation source-pulse of radiation-mask-window-prepackaged article system of elements employed in simultaneously forming non-deposited, non-destructive markings on both a prepackaged article and a window that is markingly associated therewith according to the present invention.

FIG. 4 is a plan view of a single package wherein each of a plurality of prepackaged articles, and its associated window, is marked with unique information.

FIG. 5 is a cross-sectional view taken along line 5—5 in FIG. 4.

DETAILED DESCRIPTION OF THE PREFERRED EMBODIMENTS

Figure 6:
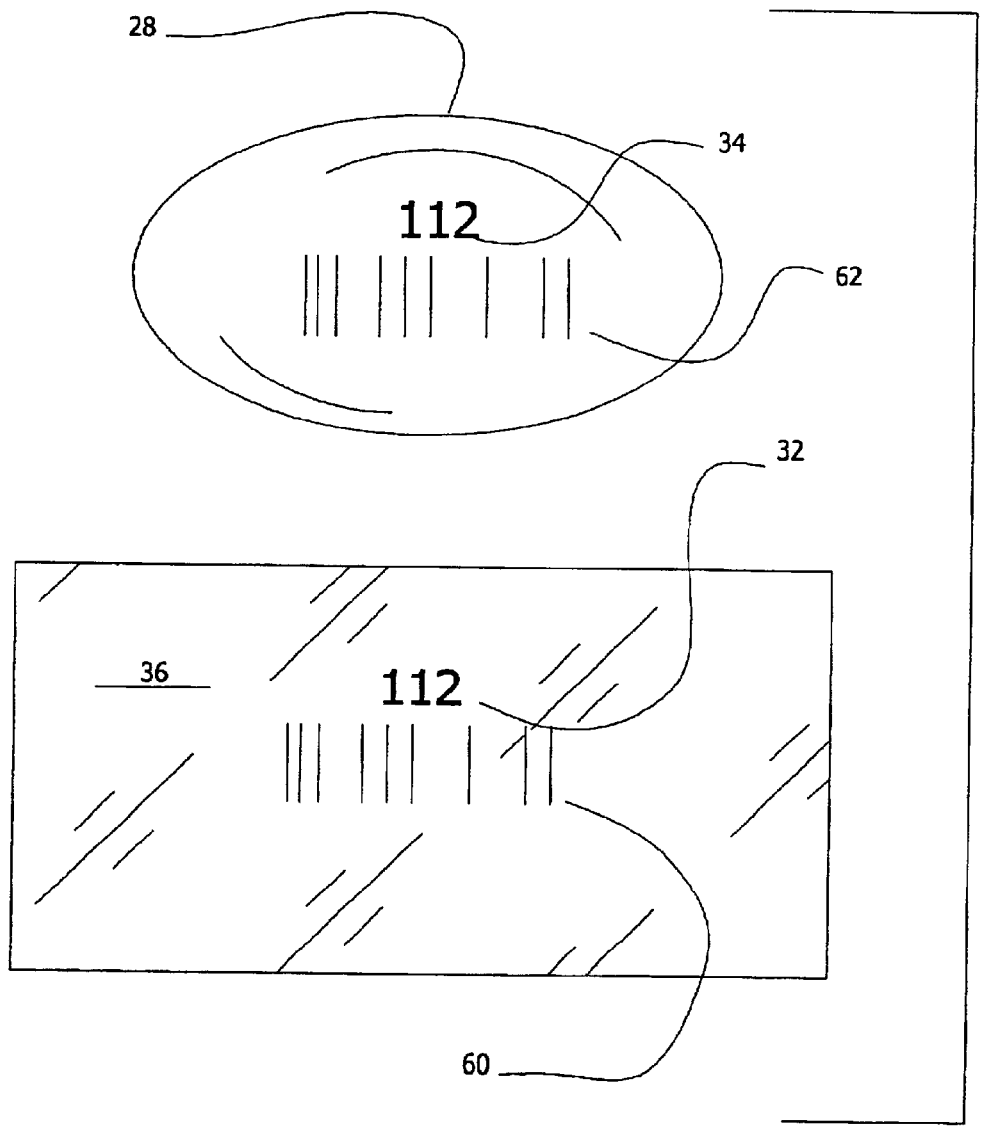
FIG. 6 is an exploded diagramatic view of one of the prepackaged articles shown in FIGS. 4 and 5, and its associated window illustrating that the identical markings appear on both the window and the article.

Referring particularly to the drawings there is schematically illustrated generally at 10 a consumable article laser marking system. The marking system comprises ultraviolet laser 12, a mask 14 in the configuration to allow the passage of a predefined pattern of ultraviolet energy, and sensor 16. The sensor 16 establishes a sensing location generally shown at 18. Consumable articles, for example, pills 20 are placed in continuous motion to travel through the sensing location 18. The sensor detects the presence of a consumable article as it passes through the sensing location 18 and, nearly instantaneously, sends a signal to the laser that an object is in the marking zone. The laser then emits a burst of coherent ultraviolet energy. The beam of energy passes through mask 14 and exposes article 20 to pattern of laser energy that is defined by mask 14. Pulsing the laser at 20 Hertz (Hz) permits the marking of up to 20 pills per second. Pulsing the laser at 200 Hertz permits the marking of up to about 200 pills per second. Alternatively, conveyor 22 carries the articles 20 through the sensing location 18.

FIG. 3 schematically illustrates a marking station indicated generally at 150 arranged to carry out the method of the present invention. A source of marking radiation 154, is provided by radiation emitter 152. A rapidly rotating mask 156 is provided with various radiation transparent openings 158. Mask 156 rotates about an axis that is generally parallel to the direction of the beam of marking radiation 154. The mask 156 rotates, for example, at from approximately 10,000 to 100,000 revolutions per minute so that all of the radiation transparent openings are frequently in position to be utilized in forming a desired pattern. The radiation emitter delivers pulses of marking radiation 154 with durations of, for example, 20 nanoseconds when a desired opening is in position to form part or all of the desired pattern of markings on the prepackaged article. With a pulse of marking radiation that only lasts for 10 to 20 nanoseconds, the mask is essentially stationary for the duration of the pulse even when it is rotating at 100,000 revolutions per minute. The marking radiation 154 passes through the mask and simultaneously marks both the marking window 160 and the prepackaged article 162 in the pattern defined by the mask. Even if the prepackaged article is moving and several different pulses of marking radiation with several differently configured openings are required to form the entire desired marking pattern, the prepackaged article is moving so slowly, compared to the duration of the pulse and the speed at which the mask rotates, that it is essentially stationary for the entire marking process. The window 160 and the prepackaged article 162 are markingly associated with one another so that one pulse of radiation forms substantially the same pattern on both. The marking occurs simultaneously and from the same pulse of radiation although several pulses with the mask in different positions to form different parts of the pattern may be required to form the full desired marking. Preferably, the marking on each of the marked objects is in substantially the same pattern, although they may be of a different intensity and detectability.

Both the window 160 and the prepackaged article 162 contain radiation sensitive marking material with which the beam of radiation 154 interacts to form the desired marking. The radiation sensitive marking material need not be the same in both the window and prepackaged article. In general, the concentration of the marking material will be different between the window and the article. The concentration of the radiation sensitive marking material in the window is generally less than in the article so the marking in the window is generally lighter than in the article. Thus, the window is at least semi-transparent to the marking radiation. Marking of the window is achieved at least in part because the window, being first in line, receives more radiation than the article. If desired, the radiation sensitive marking material in one or the other can be more sensitive to the marking radiation.

The prepackaged article is visible, at least to the marking radiation, and preferably to the human eye, through the window. The window generally forms part of the packaging for the article. The marked window may, if desired, be separable from the rest of the package without breaching the seal on the package. It may, for example, be desirable to separate the marked window from the package for record keeping purposes before or at the time that the package is opened. An adhesive backed window, for example, permits the window with the markings thereon to be removed from the package and applied to a patient's chart in a hospital without breaching the sterile package. A separable window can be used, for example, for record keeping purposes at the site of manufacturing, or at one or more locations along the chain of distribution. One or more superimposed windows for a single article can be provided so long as sufficient radiation energy gets through the multiple windows to mark the article within the package. As used in this specification and the attached claims, "window" is intended, unless otherwise indicated, to include more than one window.

The markings are preferably, but not necessarily, detectable by the unaided human eye. Detection enhancements can be used, if desired. For example, a radiation sensitive material that fluoresces under ultraviolet light can be used. The marking radiation can either activate or deactivate the fluorescent capacity of the marking material. When the applied marking radiation deactivates the fluorescent response of the marking material, the imposed pattern does not fluoresce while the surrounding material does. This produces a negative image effect. The use of marking materials in at least one of the marking pair of window-article, which are not detectable without the aid of, for example, ultraviolet light has the advantage of being undetectable to someone who tampers with the package. The unsophisticated tamperor does not know that the tampering will be detected unless the article is placed back in exact alignment with the window. Without the enhancement provided by the required viewing aid, the tamperor would not be able to place the article back in alignment with the window.

As used in this specification and the accompanying claims, unless otherwise indicated, the terms "detectable" and "detectably" include markings that require some enhancement to be visible to the human eye. The scale of the markings should be such that they are visible to the unmagnified human eye. Markings that require a magnification of more than, for example, approximately 5× for detection are prone to error. The marking process is most efficient when the articles are moving at a fairly high rate of speed past the marking station. Some slight blurring takes place because of this motion. Without magnification, this blurring is usually not detectable, and, in any event, not sufficient to impair the readability of the pattern of markings. Also, the nature of the materials is such that some occasional slight blurring is inherent in the system. When the scale of the markings is reduced, these imperfections become significant in impairing the readability of the markings. The markings should be detectable at the macro level whether other detectability enhancement is required or not.

Several articles can be packaged in one package, and different markings, for example, individual serial numbers, can be applied on the different prepackaged articles. A plurality of prepackaged articles in one package is illustrated particularly in FIGS. 4 and 5. A package with a plurality of prepackaged articles is indicated generally at 24. Blister packs, of which those indicated at 30 are typical, are sealed to a common base board 26. The top or outer panels of the illustrated blister packs provide individual marking windows 36, 40, 46, and 54, respectively through which tablets 28, 42, 48, and 52 are visible to the marking radiation, and preferably also, but not necessarily, to the human eye. The markings indicated at 50, 44, and 38 appear as one mark, but they are actually two marks, one on each of the marked pair, that is, on the window and the markingly associated article. This is illustrated particularly in FIG. 5, where the location of the marking 32 on the window is separated from the marking 34 on the article 28.

Figure 9:
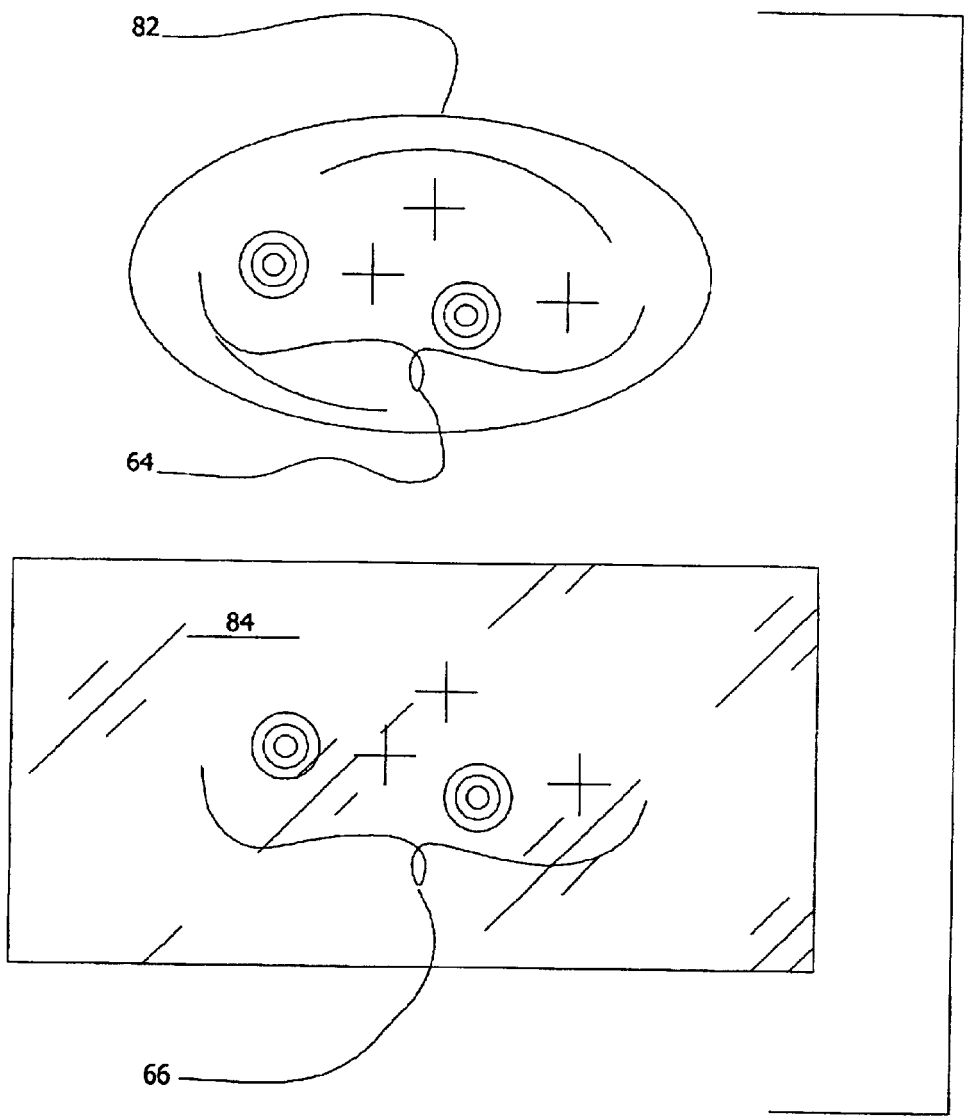
FIG. 9 is an exploded diagramatic view of a prepackaged article and its associated window illustrating the use of alignment identification markings for security purposes.

When the window and article are separated, as illustrated in FIGS. 6 and 9, it is apparent the substantially the same pattern of marking occurs on both the article and the markingly associated window. In FIG. 6, for example, the article 28 is shown separated from the article 36. An individual serial number 34 appears on article 28. The substantially identical serial number 32 appears on the associated window 36. Likewise a bar code 62 appears on the article 28, and a bar code 60, with substantially the identical pattern appears on window 36. The bar codes 60 and 62 serve to identify the type or model of article, while the individual serial numbers 32 and 34 serve to uniquely identify the exact article 28. These markings also serve as security markings. If the package is tampered with so as to disturb the seal, it would be very difficult to get the article 28 back so the markings on it align exactly with those on the window 36. Some markings are intended specifically to visually indicate when tampering occurs. See, for example, FIG. 9 where an article 82 is marked with a pattern of security markings 64. The markings 64 on article 82 are in substantially the same pattern as markings 66 on window 84. The nature of the respective markings is such that it is very difficult to get them back into registry once they have been separated or disturbed. Any misalignment along any axis is readily apparent. Thus, the integrity of the package is visible at a glance. This is particularly significant when articles must be kept sterile and only used once, or the articles are intended for internal consumption by a living being. A combination of security, serial number, model number and other markings can be used, if desired.

Figure 7:
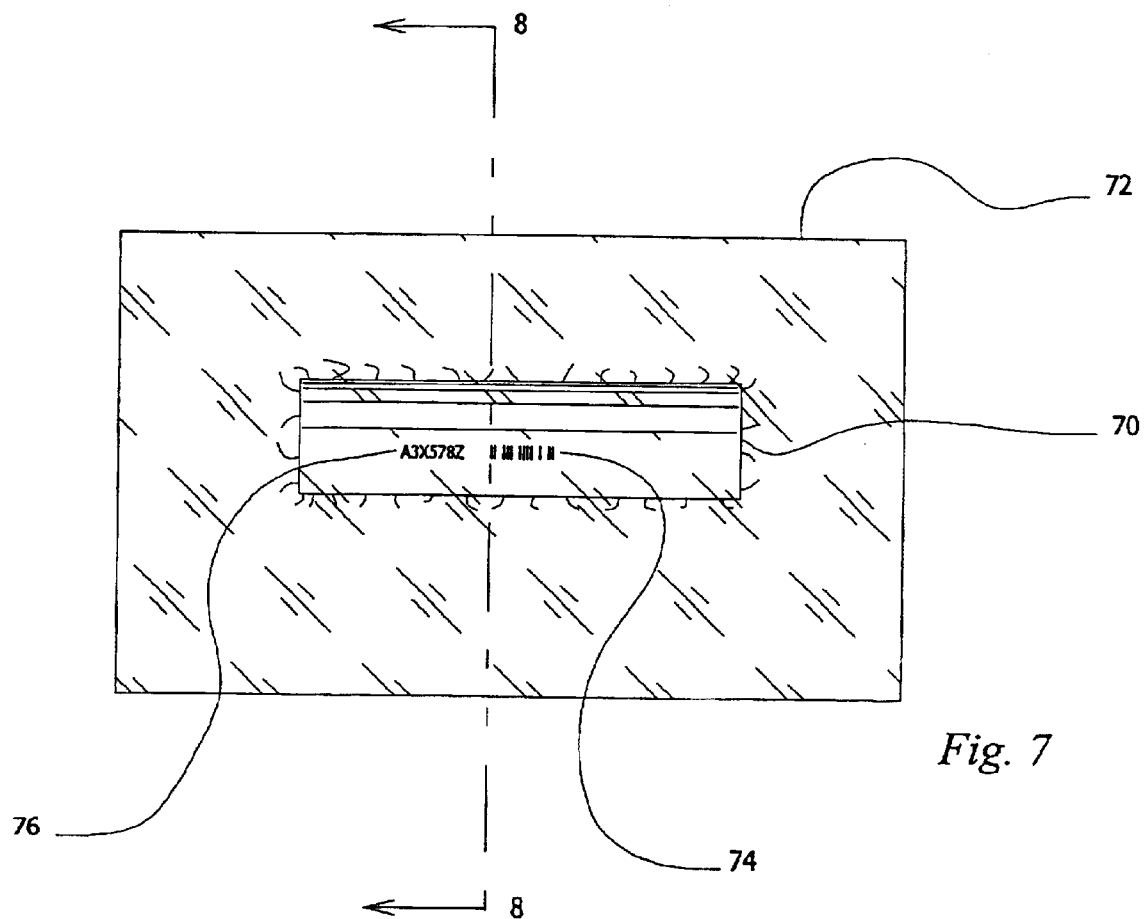
FIG. 7 is a plan view of a shrink wrapped article illustrating the simultaneous provision of markings on both the article and the markingly associated window, which markings include an identifier that is unique to the individual article, and a type or model indicator.
Figure 8:
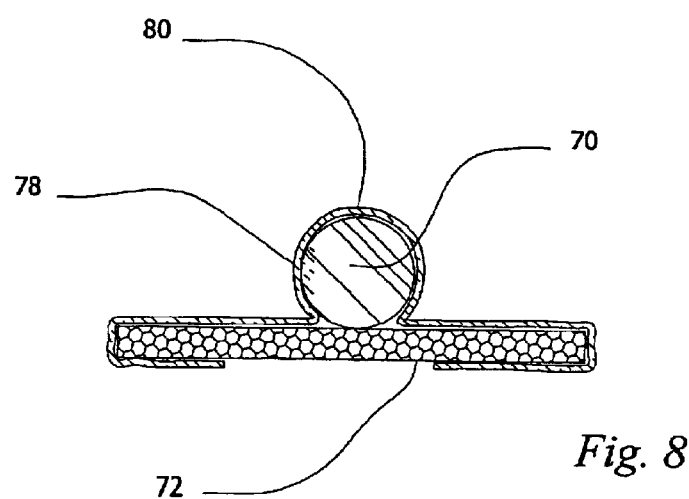
FIG. 8 is a cross-sectional view taken along line 8—8 in FIG. 7.

A shrink wrap package is illustrated particularly in FIGS. 7 and 8. A base board 72 supports an article 70. Article 70 is mounted to base board 72 by a shrink wrap 78. Shrink wrap 78 closely follows the contour of article 70 so that the marking window 80 is in contact with the associated marking surface of article 70. The pattern of the marking includes both a bar code 74 and a serial number 76, so that the prepackaged article is identified both as to its type or model, and its own unique identity. The many uses for bar codes and serial numbers are well known to those skilled in the art, and need not be elaborated on here.

Figure 10:
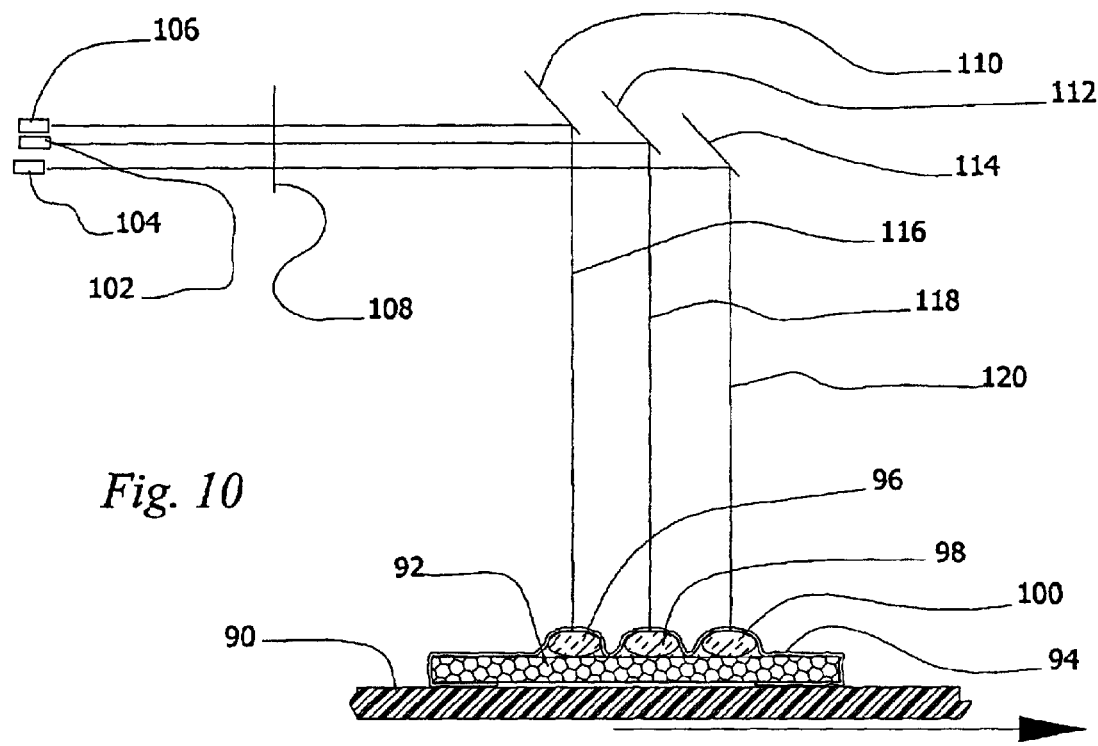
FIG. 10 is a diagramatic view illustrating the marking of a plurality of moving prepackaged articles.
Figure 11:
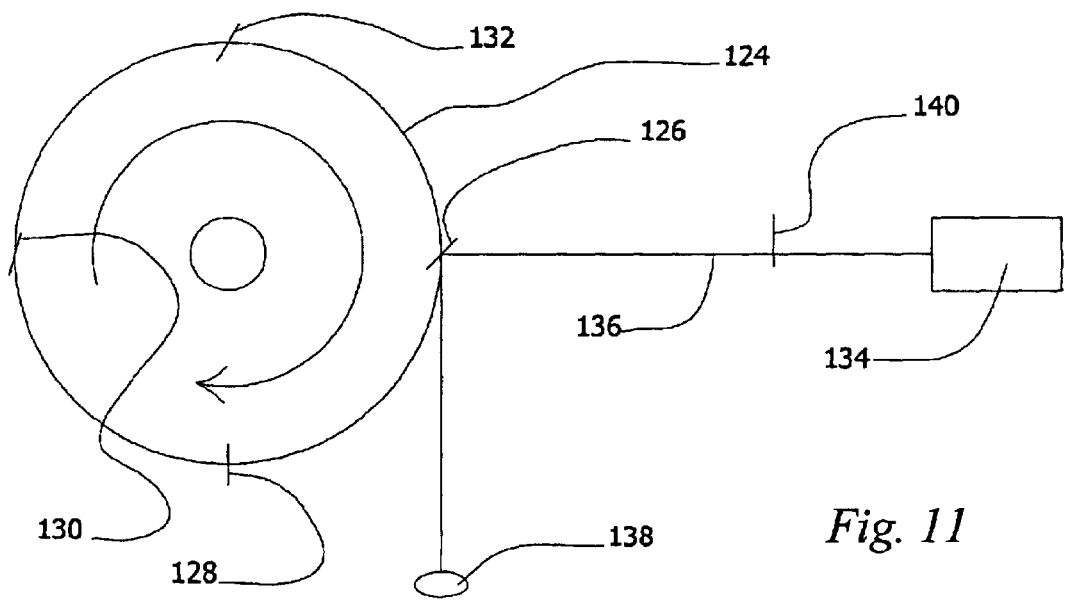
FIG. 11 is a diagramatic view illustrating an additional method of applying markings to articles according to the present invention.

The marking of multiple articles in a common package while the package is in motion is illustrated, for example, in FIGS. 10 and 11. A conveyor 90 is placed in motion as illustrated in FIG. 10. A package, which includes base board 92, shrink wrap 94 and articles 96, 98 and 100, is supported on conveyor 90. The location of the package relative to a marking station is detected by conventional sensor means, not illustrated. The marking station includes a plurality of marking radiation sources, indicated, for example, at 102, 104, and 106. These sources may emanate from one common or multiple generators. Energy from a common source can be divided, for example, by a conventional beam splitter. Separate sources can be provided, as may be desired. A pattern generating mask 108 is provided inn operative association with the marking radiation. The output from the radiation source is deflected by mirrors 110, 112, and 114 to the desired location for marking to take place. Energy reflecting mirrors 112, 110, and 114 can be stationary or moveable, as may be desired, to project the marking radiation 116, 118, and 120 onto the desired location. Multiple moving articles 96, 98, and 100 can be marked simultaneously or sequentially, as may be desired. The movement of the packaged articles and/or the movement of the energy beam are synchronized so that the packaged article is in the proper location for marking when the energy beam is emitted. Each of the windows in shrink wrap film 94, and the article that is markingly associated with that window are marked simultaneously by the same pulse of marking radiation. The windows are at least translucent to the marking energy so that at least a sufficient amount of energy reaches the article to form a detectable marking. The pulses of energy 116, 118, and 120 are so short in duration, for example, 10 to 20 nanoseconds, that even when the conveyor 90 is carrying the package at 500 hundred feet a minute or more, the package is essentially stationary for the duration of the pulse of marking radiation. Very high rates of production can be achieved according to the present invention. The electronic controls for controlling the operation, including positioning the packages, and coordinating the marking operation with the operation of the pulse emitter are conventional, and will not be further described here.

An alternative marking system is illustrated, for example, in FIG. 11. A rapidly, rotating wheel 124 includes several energy reflecting elements, such as, for example, mirrors, 126, 128, 130, and 132. The energy reflecting elements are set at different angles so that a pulse of marking energy will be precisely directed to different locations depending upon the angular position of the wheel 124 at the time the pulse of marking energy is emitted, and the angle at which the reflector is set. Wheel 124 can be rotated at a very high rate, for example, from approximately 1,000 to 100,000 revolutions per minute, more or less. A single source of marking energy 134, in operative association with a marking mask 140, can be utilized to rapidly mark a plurality of moving prepackaged articles, a typical one of which appears at 138, whether they are in common or different packages. A slight change in the angular position of wheel 124 moves mirror 126 so that the beam of marking energy 136 is directed from where it is shown in FIG. 11 to the location of the next article to be marked. If energy reflector 126 moves beyond the location where it can direct the marking energy to the desired article, in approximately one-quarter of a rotation, reflector 132 will be in position to direct a pulse of marking radiation to the desired article and associated window, not shown.

FIGS. 10 and 11 are illustrative, but not exhaustive of the possible marking systems that can be used to marking moving prepackaged articles. Various other systems or combinations of systems can be employed, as will be understood by those skilled in the art.

Figure 12:
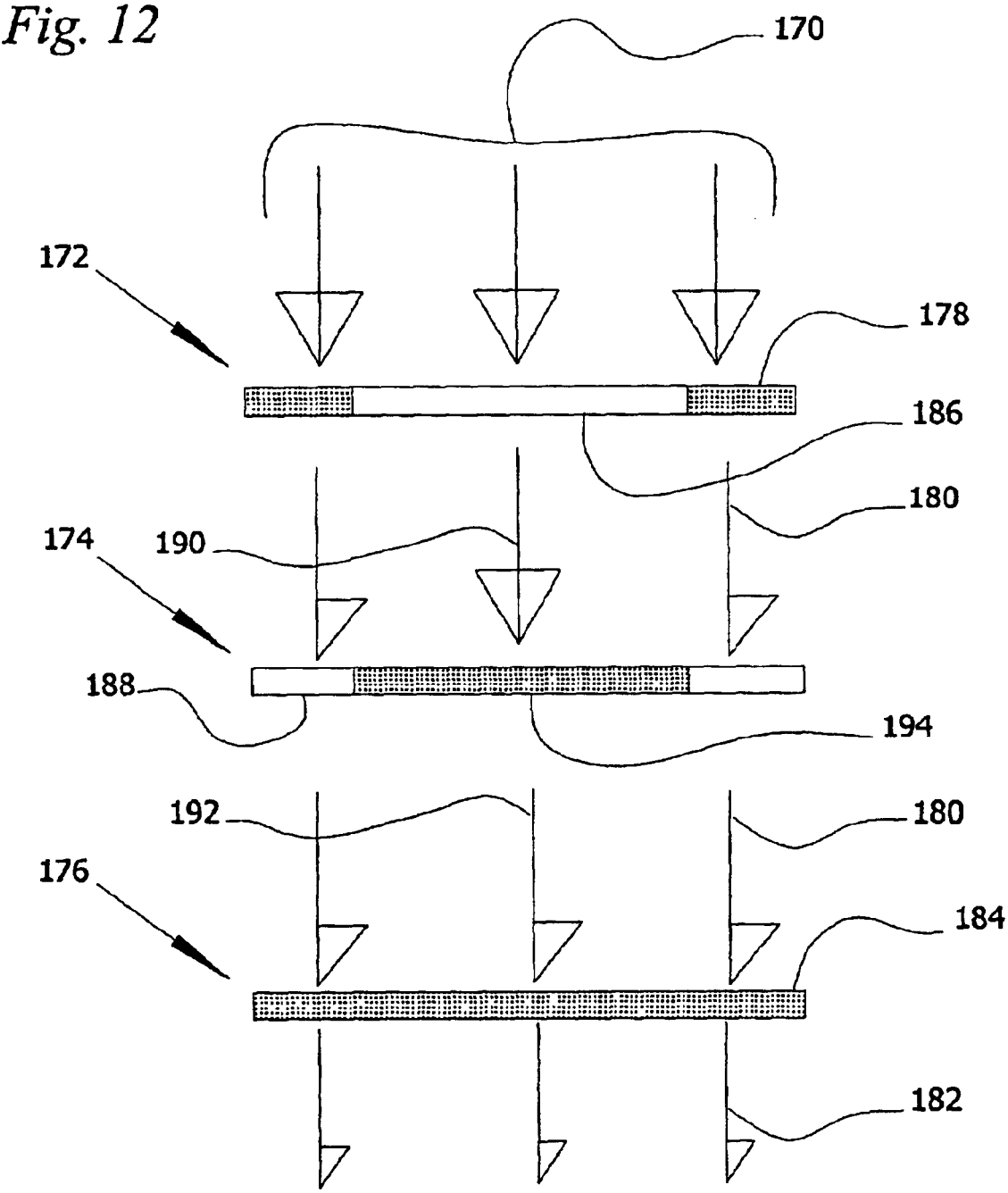
FIG. 12 is a diagramatic view illustrating the simultaneous marking of a plurality of windows and an article where the marking is distributed between two windows.

FIG. 12 is illustrative of the marking of an article wherein a plurality of marking windows are provided for one article, and the marking is distributed between the plurality of windows. A substantially uniform pulse of marking energy or radiation is indicated at 170. First window 172 has two regions, one of which is indicated at 178, which are capable of generating or forming a detectable mark when subjected to radiation 170. The region 186 between these two regions does not contain any radiation sensitive material so no mark is formed there. The radiation passes through the unmarked region 186 of first window 172 substantially unchanged, as illustrated at 170 and 190. Some of the energy that falls on the region 178 is expended in causing the radiation sensitive material to change to a detectable marking. The thusly diminished pulse of energy is indicated at 180. Second window 174 includes one central region 194, which contains radiation sensitive marking material. The region 188 of of window 174 is substantially transparent to the pulse of radiation. The radiation transparent regions 186 and 188 of first window 172 and second window 174, respectively, are not in registry with one another, so the markings in first window 172 and not the same as those in second window 174. As indicated at 180 and 190, the pulse of energy passes through the transparent regions of the first and second windows 172 and 174 substantially unchanged. The energy that is expended in forming a mark diminishes the energy that passes through the respective windows. The article 184 includes a substantially uniform distribution of radiation sensitive marking material at least in the area that is markingly associated with the windows 172 and 174. Where, for example, a thin article such as that illustrated at 176, is marked, there may be enough energy in the pulse 170 to pass through the article, see 182, so as to mark yet another window (not illustrated) on the opposed side of the article. Typically, the pulse of energy is fully absorbed within the article. The quantity of energy in the pulse is adjusted to achieve the desired marking on the last item to be marked.

Transparent region 186 can be provided adjacent to markingly sensitive region 178 in first window 172 by, for example, forming them separately and joining them edge to edge or in an overlapping relationship. Such techniques are well known in the arts are need not be further described here.

The windows and the article are shown widely separated for purposes of illustration in FIG. 12. Typically, they are located in close or touching proximity to one another.

The arrangement illustrated in FIG. 12 can be used, for example, where window 172 is to be removed for some purpose, such as inventory control, channel of distribution, or routing information, and window 174 remains with the article 176 until it is used. The omission of critical information, such as a serial number, from the removable window prevents counterfeiting by depriving those who just handle the first window 172 of critical information that would be needed for successful counterfeiting. First window 172 is not needed to protect the integrity of, for example, a sterile prepackaged article 184.

Numerous lasers are available that can be operated in the ultraviolet region. Where high production rates in excess of 200 articles per second or more are required, ultraviolet excimer lasers, for example, can be used. Various fixed and moving masks can be used, as desired. Due to the very short pulse duration, consumable articles can be marked on the fly, that is, while continuously moving at high rates of speed through the marking zone. The length of the pulse compared to the velocity of the article is such that the article is essentially frozen in place during the pulse. The instantaneous position of the article does not change enough during the marking step to cause any perceptible blurring of the marking. Various article feed mechanisms can be used. Where high rates of production are required, gravity feed may not be fast enough. The articles to be marked must be accelerated to speeds that will accommodate high production rates. Marking at even very high rates of production, for example, 400 articles per second, can be achieved at high resolution and with little or no scrap rate.

Marking is achieved when titanium dioxide absorbs energy that is emitted in the ultraviolet region, undergoes a photochemical change, and turns from white to black. Most significantly, titanium dioxide is also generally regarded as safe for human consumption. The amount of energy in the ultraviolet wavelengths, which is effective to cause the titanium dioxide to change color, is substantially completely absorbed by the titanium dioxide. Energy in other parts of the spectrum, for example, the infrared, would cause heating to a much greater depth and over a much wider area with the potential for damaging the pill through physical degradation. Preferably, the ingredients in the marking layer, other than the titanium dioxide, are substantially transparent to the radiation. Also, to the extent possible the rest of the article should be transparent to the radiation, although it can be, for example, reflective of the ultraviolet radiation.

In the preferred embodiment that has been selected for purposes of illustration only and not limitation, consumable articles having an effective amount of titanium dioxide in their outer surface layer, about 2 percent by weight of the outer layer, provide satisfactory marking results when exposed to ultraviolet laser energy at a wavelength of 355 nanometers, a pulse rate of 20 Hertz, a pulse duration of 10 nanoseconds, and a pulse energy of 20 milliJoules optically condensed to give a density of about 1 Joule per square centimeter of the marked area. In general, the amount of titanium dioxide is preferably limited to that which is effective to produce the desired visible marking. Excess amounts serve no useful purpose, and can be detrimental. Preferably, the titanium dioxide need only be present in an effective amount in the layer of the articles where marking is to occur, but may be present throughout the entire volume of the article, if desired. The thickness of the layer that contains the effective amount of titanium dioxide need only be a few mills thick, if desired.

It is unclear why ultraviolet laser energy, when applied to articles containing titanium dioxide, produces clear and sharp markings. Although applicant does not intend to be limited to any theory, it is believed that the ultraviolet laser energy, when delivered to the titanium dioxide at a wavelength that it can absorb, and for a very short time duration yet at a high power level, causes some structural modification to the titanium dioxide molecules, and this structural modification is visibly detectable as a change in color. It is not believed that the laser energy burns the material that surrounds the titanium dioxide since the time duration of exposure is so small, and also because no holes or voids are present on the surface of the articles when viewed with an optical microscope at a magnification factor of 5×.

In one embodiment, a Nd:YAG pulse laser is used. In this embodiment, in which the laser operated at 20 Hz, consumable articles are capable of being marked at a rate of about 1,200 per minute (720,000 per hour). This marking rate is competitive with conventional ink deposition marking systems.

It is to be appreciated that other lasers can be used, as desired, for purposes of increasing the marking rate. For example, an Xe:Cl excimer laser may be used, as desired, operating at up to as much as 400 Hz. Utilizing such a laser at 400 Hz provides the potential to mark the consumable articles at 24,000 per minute, (1,440,000 per hour) which is many times faster than the conventional prior art ink deposition marking systems. For example, the LPX 100i series Xe:Cl excimer laser, produced by Lambda Physik Inc., operating at 400 Hz and producing 100 milliJoules of laser energy at a wavelength of 308 nanometers, could easily achieve the substantially increased marking rates discussed above. Other lasers may be used, as desired, such as solid state lasers (i.e. Nd:YAG, or Nd:YFL), or gaseous excimer lasers (XeCl, KrF, ArF, or F2), as long as the wavelength, energy density, and pulse duration, are effective to produce the desired marking.

The rate at which the target articles are moving in the marking zone is so slow, even at a rate of 400 articles per second, compared to the duration of the laser pulse, that the target articles are assumed to be stationary at the time of marking. Thus, the articles can be moving at a constant rate, or they can be accelerating or decelerating without having any significant impact on the quality of the marking. The efficiency of the system depends in significant part on the fact that the target articles can be marked while they are in motion, and without elaborate positioning procedures and equipment. Preferably, the marking area of the target article is substantially perpendicular to the beam of energy, although misalignment of as much as, for example, 10 degrees, more or less, can be tolerated without rendering the marking unintelligible due to distortion. Even at greater angles the marking will still occur, but it may be so distorted that it is not easy to read. Since there is no physical impact required to accomplish the desired marking, the target article need not be supported in any way. That is, it is free standing. Thus, it is feasible to mark an article while it is in free flight under the influence of gravity or after it has been discharged from a projecting device.

Occasionally, products are made in two or more parts that are separated during use, for example, a sheath and a tool that goes in the sheath, or the like. For various reasons, including, for example, safety and utility, such separable components may need to be reassembled to one another in a particular relationship. Providing identical or matching markings on the respective parts, according to the present invention, facilitates such reassembly. Thus, the terms, "packaging", "packaging material", "package", "window", "marking window", and the like, unless otherwise indicated, includes separable components that are functionally associated with the prepackaged article in use, and are frequently intended to be reassemblable with the article. These terms are not limited to just those materials that are intended to be discarded, and the markings are not limited to serving a single or one time purpose. The markings can serve multiple functions at different times.

For the purposes of description herein, reference has been made particularly to the simultaneous marking of two superimposed objects. As will be understood by those skilled in the art, more than two objects can be marked simultaneously, so long as the energy used to accomplish the marking does not visibly degrade either object. The marking energy is typically absorbed in the article, but where the energy is sufficient to pass entirely through the article, the packing or a second article can also be marked. Some percentage of the radiation is absorbed in each object until what is left is insufficient to make a detectable marking.

Certain products are of such a critical nature that it is necessary to provide a trace of every entity that has handled it. Conventionally, this has been accomplished by recording the fact that the article has passed through a particular entity's control by hand or in an electronically created database, as, for example, by passing the article through a bar code reader. According to the present invention, the article and associated packaging can be marked by more than one entity at different times, and at different locations. Thus, the packaged article bears markings that provide the full history of its travels between entities at one glance. Also, a particular article may be associated with a particular entity. For example, a particular medication can be marked in a hospital with the ID of a particular patient without opening the package. This finds particular application in the administration of experimental drugs.

What have been described are preferred embodiments in which modifications and changes may be made without departing from the spirit and scope of the accompanying claims. Many modifications and variations of the present invention are possible in light of the above teachings. It is therefore to be understood that, within the scope of the appended claims, the invention may be practiced otherwise than as specifically described.

What is claimed is:

1. A method of simultaneously forming detectable non-deposited markings on a discrete consumable article and on packaging material therefor, said discrete consumable article being intended for consumption by a living being for therapeutic purposes, comprising the steps of:

providing a marking window in said packaging material;

including an amount of radiation sensitive material in both said marking window and said discrete consumable article, said amount of radiation sensitive material being sufficient to permit an ultraviolet laser energy to simultaneously form said detectable non-deposited markings on both said marking window and said discrete consumable article, said marking window being sufficiently transparent to said ultraviolet laser energy to permit said ultraviolet laser energy to pass therethrough and form said detectable non-deposited markings on said discrete consumable article;

providing a source of said ultraviolet laser energy;

interposing said marking window between said source and said discrete consumable article;

simultaneously exposing said discrete consumable article and said marking window to said ultraviolet laser energy in a predefined pattern to form said detectable non-deposited marking in said predefined pattern on both said marking window and said discrete consumable article, said step of simultaneously exposing to said ultraviolet laser energy being insufficient to cause visible physical degradation to said marking window and said discrete consumable article when viewed at no more than about 5 power magnification.

2. A method of claim 1 wherein the step of including comprises including an effective amount of titanium dioxide in at least one of said marking window and said discrete consumable article.

3. A method of claim 1 wherein the step of including comprises including effective an amount of titanium dioxide in both said marking window and said discrete consumable article.

4. A method of claim 1 wherein said interposing includes packaging a plurality of said discrete consumable articles in one package.

5. A method of claim 1 including placing said discrete consumable article and said marking window in motion, and the step of simultaneously exposing is accomplished while said marking window and said discrete consumable article are in motion.

6. A method of simultaneously applying a non-destructive marking on both a prepackaged article and a window of packing material associated with said prepackaged article, said window of packing material being at least semi-transparent to marking radiation, said method comprising:

packaging an article in packaging material to position said window of packing material in marking association with said prepackaged article;

providing radiation sensitive marking material in said window of packing material and in said prepackaged article, said radiation sensitive marking material being adapted to change detectably when exposed to said marking radiation;

projecting an instantaneous pulse of said marking radiation having a predetermined pattern through said window of packing material onto said prepackaged article;

exposing said window of packing material and said prepackaged article to an amount of said marking radiation that is sufficient to cause the radiation sensitive marking material in both the window of packing material and the prepackaged article to change detectably in said predetermined pattern, said predetermined pattern being detectable in both said window of packing material and said article, said amount of marking radiation being limited to an amount required to cause said radiation sensitive marking material to change detectably without causing visible physical degradation of either said window of packing material or said prepackaged article when viewed at no more than about 5 power magnification.

7. A method of claim 6 wherein said prepackaged article is a medical device.

8. A method of claim 6 wherein said prepackaged article is a consumable article intended for consumption by a living being for therapeutic purposes.

9. A method of claim 6 including providing an array of said prepackaged articles in a single package with a said window of packing material in marking association with each of the prepackaged articles in said array, and projecting said instantaneous pulse through each of said windows of packing material onto each of said prepackaged articles.

10. A method of claim 6 including projecting a plurality of said instantaneous pulses through said window of packing material onto said prepackaged article to form said predetermined pattern.

11. A method of claim 6 wherein said predetermined pattern is in the form of at least a bar code.

12. A method of claim 6 wherein said predetermined pattern is substantially the same in both said window of packing material and said article.

13. A method of claim 6 wherein said predetermined pattern is in the form of at least an alignment indicator, said alignment being adapted to providing a visible indication if said prepackaged article has been tampered with.

14. A method of claim 6 wherein said radiation sensitive material is of substantially the same composition in both the window of packing material and the prepackaged article, and said projecting comprises projecting ultraviolet laser energy.

15. A method of simultaneously applying a non-destructive marking on both a prepackaged sterile article and a window of packing material associated with said prepackaged sterile article, said window of packing material being at least semi-transparent to marking radiation, said method comprising:

providing a sterile article;

packaging said sterile article in packaging material to provide said prepackaged sterile article in a sterile environment, said packing material including a window through which said sterile article is visible;

providing radiation sensitive marking material in said window and in said sterile article, said radiation sensitive marking material being adapted to change detectably when exposed to said marking radiation; and projecting an instantaneous pulse of a pattern of said marking radiation through said window onto said prepackaged sterile article while maintaining said sterile environment, and allowing said radiation sensitive marking material to change detectably in said pattern in both said window and said sterile article without causing visible physical degradation to either said window or said prepackaged sterile article when viewed at no more than about 5 power magnification.

16. A method of simultaneously applying substantially the identical pattern of non-destructive marking on both a prepackaged article and packing material associated with said prepackaged article, said method comprising:

providing an article;

packaging said article in said packing material to provide said prepackaged article, said packing material including a window through which said article is visible;

providing radiation sensitive marking material in said window and in said prepackaged article, said radiation sensitive marking material being adapted to change detectably when exposed to marking radiation; and applying said non-destructive marking simultaneously to each said prepackaged article and said window, said applying including projecting an instantaneous pulse of marking radiation through said window onto said prepackaged article, and allowing said radiation sensitive marking material to change detectably in both said window and said prepackaged article.

17. A method of simultaneously applying a non-destructive marking of claim 16 including providing a plurality of prepackaged articles in a single package, said single package including a said window associated with each of said prepackaged articles.

18. A method of simultaneously applying a non-destructive marking of claim 16 including placing said prepackaged article in motion and applying said non-destructive marking as said prepackaged article is in motion.

19. A method of simultaneously applying a non-destructive marking of claim 16 including providing a plurality of prepackaged articles in a single package, said single package including said window associated with each of said prepackaged articles, said applying including applying at least a unique said non-destructive marking to each of said plurality of prepackaged articles.

20. A method of simultaneously applying a non-destructive marking of claim 16 including providing a plurality of prepackaged articles in a single package, said single package including a said window associated with each of said prepackaged articles, said applying including applying at least a substantially identical said non-destructive marking to each of said plurality of prepackaged articles.

21. A method of simultaneously applying a non-destructive marking of claim 16 including providing a plurality of prepackaged articles in a single package, said single package including a said window associated with each of said prepackaged articles, said applying including applying at least both a unique and a substantially identical said non-destructive marking to each of said plurality of prepackaged articles.

22. A discrete consumable article enclosed within a package, said consumable article being intended for consumption by a living being for therapeutic purposes, said package including a marking window positioned adjacent to said discrete consumable article, said discrete consumable article comprising from about 0.5 to 5 weight percent of titanium dioxide, said titanium dioxide having an average particle size of less than about 10 microns, said titanium dioxide being in a visible layer of said discrete consumable article, except for said titanium dioxide said visible layer being substantially inert to ultraviolet radiation, said titanium dioxide having a first color, a portion of said titanium dioxide in a predefined pattern having a different color from said first color, said different color being formed in situ in said visible layer in a first region on said discrete consumable article, said marking window including an ultraviolet radiation sensitive material, said ultraviolet radiation sensitive material having an initial color, a portion of said ultraviolet sensitive material in a second region being formed in a predetermined pattern corresponding to and substantially in registry with said predefined pattern and having a different color from said initial color, said consumable article and said marking window exhibiting no physical degradation in said first and second regions when viewed at no more than about 5 power magnification.

23. A discrete consumable article enclosed within a package, said consumable article being intended for consumption by a living being for therapeutic purposes, said package including a marking window positioned adjacent to said discrete consumable article, both said discrete consumable article and said marking window including marking material that is sensitive to radiation, a portion of said marking material in each of said marking window and said discrete consumable article being formed into a detectable predefined pattern, each of the detectable predefined patterns being substantially identical and formed in situ, said detectable predefined patterns being positioned substantially in registry with one another, and said detectable predefined patterns exhibiting no physical degradation when viewed at no more than about 5 power magnification.

24. A discrete consumable article of claim 23 wherein said detectable predefined patterns have detectable properties, said detectable properties being of a character formed responsive to exposure to said radiation.

25. A discrete consumable article of claim 23 wherein, except for said marking material, said marking window and said discrete consumable article being substantially inert to said radiation.

26. A discrete consumable article of claim 23 wherein said marking material in said discrete consumable article comprises titanium dioxide.

27. A physical article enclosed within a package, said package including a marking window positioned adjacent to said physical article, both said physical article and said marking window including marking material that is sensitive to radiation, a portion of said marking material in each of said marking window and said physical article being formed into a detectable predefined pattern, each of the detectable predefined patterns having detectable properties, said detectable properties being of a nature formed by exposure to said radiation, said detectable predefined patterns being substantially identical and formed in situ, said detectable predefined patterns being positioned substantially in registry with one another, and said detectable predefined patterns exhibiting no physical degradation when viewed at no more than about 5 power magnification.

28. A physical article according to claim 27 wherein said marking material in said physical article comprises titanium dioxide.

29. A physical article according to claim 27 wherein said marking window is held in a fixed location to and in physical contact with said physical article.

30. A physical article according to claim 27 wherein said physical article is a medical device and said package is adapted to maintain said medical device in a sterile condition.

31. A prepackaged article in a package, both said prepackaged article and package having substantially the same non-destructive marking thereon, said prepackaged article in a package comprising:
    an article contained within packing material, said packing material being formed into said package and including a window through which said article is visible, said article and said window including marking material, said marking material being adapted to changing to a detectable form when exposed to marking radiation, said marking material in each of said window and said article exhibiting substantially identical detectable patterns, said detectable patterns defining said non-destructive marking.

32. A prepackaged article in a package of claim 31 including a plurality of prepackaged articles in said package, each of said plurality of articles including a window associated therewith, each of said plurality of prepackaged articles being visible through the window that is associated therewith.

33. An article prepackaged within a package to provide a prepackaged article, both said article and said package having substantially the same non-destructive marking thereon, said article prepackaged within a package comprising:
    packing material formed into said package, said packing material including a window through which said article is visible, said article and said window including marking material, said marking material being adapted to changing to a detectable form when exposed to marking radiation, said non-destructible markings occurring as substantially identical detectable patterns in each of said window and said article, said detectable patterns being composed of said marking material in said detectable form, said detectable form being substantially free of visible physical degradation when viewed at no more than about 5 power magnification.

34. A plurality of articles individually prepackaged within a single package, said package comprising:

packing material formed into said package, said packing material including a plurality of windows, each of said articles being visible through a said window that is associated therewith, each such associated article and window providing a marked pair, said articles and said windows including marking material, said marking material being adapted to changing to a detectable form when exposed to marking radiation, each of said marked pairs having substantially identical detectable patterns therein, said detectable patterns being composed of said marking material in said detectable form, said detectable form being non-deposited and substantially free of visible physical degradation when viewed at no more than about 5 power magnification.

35. A plurality of discrete consumable articles individually prepackaged within a single package, said discrete consumable articles being intended for consumption by a living being for therapeutic purposes, said package comprising:

packing material formed into said package, said packing material including a plurality of windows, each of said discrete consumable articles being visible through a said window that is associated therewith, each such associated discrete consumable article and window providing a marked pair, said discrete consumable articles and said windows including marking material, said marking material being adapted to changing to a detectable form when exposed to marking radiation, each of said marked pairs having substantially identical detectable patterns therein, said marked pairs being held in substantially fixed relationship to one another with said detectable patterns in each of said marked pairs being in substantial registry with one another, said detectable patterns being composed of said marking material in said detectable form, said detectable form being non-deposited and substantially free of visible physical degradation when viewed at no more than about 5 power magnification.

36. A method of simultaneously applying detectable non-deposited markings on an article and on packaging material associated therewith, said method comprising the steps of:

selecting marking material, said marking material being adapted to forming said detectable non-deposited identification markings when exposed to ultraviolet laser energy;

including an effective amount of said marking material in at least a part of said article;

providing a window in said packaging material and including an effective amount of said marking material in said window;

packing said article in said packing material so that said article is visible through said window, said packing being carried out in a clean room and said article being sealed within said packing material to provide a sealed package;

removing said sealed package from said clean room;

providing a source of said ultraviolet laser energy outside of said clean room;

exposing said article through said window to said ultraviolet laser energy in a predefined pattern without breaching said sealed package, said ultraviolet laser energy being effective to cause said marking material in said article and said window to change to said detectable non-deposited identification marking, and said ultraviolet laser energy being insufficient to cause visible physical degradation of said window and said article when viewed at no more than about 5 power magnification.

37. A method of simultaneously applying detectable non-deposited markings according to claim 36 including selecting the same marking material for including in said window and said article.

\* \* \* \* \*